(12) United States Patent
Atay et al.

(10) Patent No.: US 11,547,513 B2
(45) Date of Patent: *Jan. 10, 2023

(54) HAPTIC USER INTERFACE FOR ROBOTICALLY CONTROLLED SURGICAL INSTRUMENTS

(71) Applicant: Asensus Surgical US, Inc., Durham, NC (US)

(72) Inventors: Stefan Atay, Raleigh, NC (US); Kevin Andrew Hufford, Cary, NC (US); Paul Wilhelm Schnur, Pipersville, PA (US); Matthew R Penny, Holly Springs, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/523,529

(22) Filed: Nov. 10, 2021

(65) Prior Publication Data

US 2022/0061942 A1 Mar. 3, 2022

Related U.S. Application Data

(63) Continuation of application No. 16/513,670, filed on Jul. 16, 2019, now Pat. No. 11,179,214.

(51) Int. Cl.
| | |
|---|---|
| *A61B 34/00* | (2016.01) |
| *A61B 34/37* | (2016.01) |
| *B25J 9/10* | (2006.01) |
| *B25J 9/16* | (2006.01) |
| *A61B 34/30* | (2016.01) |

(52) U.S. Cl.
CPC ............. *A61B 34/76* (2016.02); *A61B 34/37* (2016.02); *A61B 34/74* (2016.02); *B25J 9/106* (2013.01); *B25J 9/1664* (2013.01); *A61B 2034/302* (2016.02); *G05B 2219/45117* (2013.01)

(58) Field of Classification Search
CPC ......... A61B 34/76; A61B 34/37; A61B 34/74; A61B 2034/302; B25J 9/106; B25J 9/1664; B25J 9/0045; B25J 13/025; B25J 9/1689; G05B 2219/45117; G05B 2219/40146; G05B 2219/40161; G05B 2219/40195
USPC ................. 700/245–264; 318/568.11–568.25
See application file for complete search history.

(56) References Cited

U.S. PATENT DOCUMENTS

| | | | |
|---|---|---|---|
| 6,246,200 B1 * | 6/2001 | Blumenkranz | A61B 34/70 318/568.25 |
| 6,377,011 B1 | 4/2002 | Ben-Ur | |
| 6,522,906 B1 | 2/2003 | Salisbury, Jr. | |
| 6,866,671 B2 * | 3/2005 | Tierney | A61B 34/37 606/1 |
| 7,048,745 B2 * | 5/2006 | Tierney | G16H 40/63 606/1 |
| 7,466,303 B2 | 12/2008 | Yi | |

(Continued)

*Primary Examiner* — Jaime Figueroa

(57) ABSTRACT

A powered user interface for a robotic surgical system includes a base, a handle mounted to the base and moveable relative to the base in at least six degrees of freedom, and actuators. The interface operates in accordance with a first mode of operation in which the actuators are operated to constrain predetermined ones of the joints to permit motion of the handle in only 4DOF with respect to the base, and a second mode of operation in which the actuators permit motion of the handle in at least 6DOF with respect to the base.

20 Claims, 9 Drawing Sheets

(56) References Cited

U.S. PATENT DOCUMENTS

| | | |
|---|---|---|
| 8,541,970 B2 | 9/2013 | Nowlin |
| 8,897,916 B2 | 11/2014 | Kawashima et al. |
| 8,909,370 B2 | 12/2014 | Stiehl et al. |
| 9,039,681 B2 | 5/2015 | Wang et al. |
| 9,549,781 B2 | 1/2017 | He et al. |
| 9,554,864 B2 * | 1/2017 | Taylor .................. B25J 15/0466 |
| 9,815,206 B2 * | 11/2017 | Balicki .................. A61B 34/77 |
| 10,271,914 B2 | 4/2019 | Nambi et al. |
| 10,271,915 B2 | 4/2019 | Diolaiti et al. |
| 11,065,069 B2 | 7/2021 | Kang et al. |
| 11,291,510 B2 | 4/2022 | Shelton, IV |
| 11,311,342 B2 | 4/2022 | Parihar |
| 2004/0034283 A1 | 2/2004 | Quaid |
| 2004/0111183 A1 | 6/2004 | Sutherland et al. |
| 2005/0177054 A1 | 8/2005 | Yi et al. |
| 2006/0279534 A1 | 12/2006 | Powers et al. |
| 2007/0013336 A1 | 1/2007 | Nowlin et al. |
| 2007/0018958 A1 | 1/2007 | Tavakoli et al. |
| 2009/0055019 A1 | 2/2009 | Stiehl et al. |
| 2010/0094312 A1 | 4/2010 | Ruiz Morales et al. |
| 2012/0265051 A1 | 10/2012 | Fischer et al. |
| 2013/0131867 A1 | 5/2013 | Olds et al. |
| 2014/0267626 A1 | 9/2014 | Lilagan et al. |
| 2015/0223897 A1 * | 8/2015 | Kostrzewski .......... A61B 46/10 606/1 |
| 2015/0289946 A1 | 10/2015 | Johansson et al. |
| 2015/0342695 A1 | 12/2015 | He et al. |
| 2015/0351857 A1 | 12/2015 | Vander Poorten et al. |
| 2016/0228205 A1 | 8/2016 | Nambi et al. |
| 2017/0156805 A1 * | 6/2017 | Taylor .................... A61B 90/06 |
| 2018/0199951 A1 * | 7/2018 | Chappuis ........... A61B 17/7085 |
| 2018/0200016 A1 * | 7/2018 | Chappuis ............... A61B 34/30 |
| 2018/0256259 A1 * | 9/2018 | Crawford ................ A61B 6/12 |
| 2019/0125361 A1 | 5/2019 | Shelton, IV |
| 2019/0125459 A1 | 5/2019 | Shelton, IV |
| 2019/0143513 A1 | 5/2019 | Rabindran et al. |
| 2019/0231459 A1 | 8/2019 | Mustufa |
| 2020/0405375 A1 | 12/2020 | Shelton, IV |
| 2021/0059780 A1 | 3/2021 | Sutherland et al. |

\* cited by examiner

HAPTIC USER INTERFACE FOR ROBOTICALLY CONTROLLED SURGICAL INSTRUMENTS

This application is a continuation of U.S. application Ser. No. 16/513,670, filed Jul. 16, 2019, now U.S. Ser. No. 11/179,214, issued Nov. 23, 2021.

TECHNICAL FIELD OF THE INVENTION

The present invention relates generally to the field of surgical systems using electromechanical drivers to effect movement of medical instruments within a body cavity. More particularly, the invention relates to a haptic user interface for such systems.

BACKGROUND

Surgical systems used for robotically-assisted surgery or robotic surgery employ electromechanical drivers to drive movement of surgical devices or instruments within a body cavity, typically in response to signals generated when a user moves a user input device. Examples of such systems are those shown and described in U.S. Pat. No. 9,360,934, International Publications WO 2007/088206, WO 2008 049898, and WO 2016 057989. In a typical system, movement of the surgical device is achieved by using a robotic manipulator arm to robotically reposition or reorient the surgical device and/or by causing movement of some portion of the surgical device (e.g. an instrument end effector) relative to another portion of the surgical device. Input to the system is generated based on input from a surgeon positioned at a master console, typically using primary input devices such as input handles that the surgeon moves in the way he or she might use manual surgical instrument handles when operating using manual instruments.

The number of degrees of freedom (DOFs) of motion for a robotically controlled surgical device can vary between surgical systems and also between the different devices used for a particular system. A robotically controlled rigid-shafted instrument that moves similarly to a conventional laparoscopic instrument will have the 4 DOFs of pitch and yaw (each by pivoting the rigid instrument shaft relative to a fulcrum at the incision site), axial roll about the longitudinal axis of the instrument, and translation along the longitudinal axis of the instrument (along the axis of insertion/withdrawal of the instrument relative to the incision). Additional degrees are present for devices or instruments having greater complexity. For example, an instrument that includes an elongate rigid shaft having a region that can be robotically controlled to articulate or bend can have additional DOFs in the region of the articulation or bend. As a more specific example, such an instrument might be configured to move the instrument tip or end effector in pitch and/or yaw relative to the instrument shaft (i.e. in addition to the pitch and/or yaw that results from movement of the rigid instrument shaft about a fulcrum at the incision site), giving the instrument 6DOFs.

There are two typical types of user instrument handle motion used in surgery. In laparoscopic surgery, the instrument shafts pivot about a fulcrum at the incision site. Thus when the surgeon moves the instrument handle upwardly, the tip of the instrument moves downwardly in the body. Surgical robotic systems designed for use by laparoscopic surgeons simulate this motion, providing user interfaces having handles that move and give input in a manner familiar to the surgeons. UI handles that move in accordance with laparoscopic motion are operated in a 4DOF mode of operation in which the handle motion is often limited to yaw, pitch, roll and insertion.

Another type of instrument handle motion used in surgery is referred to as "true cartesian motion," which differs from laparoscopic motion in that there is no inversion of the motion.

Some user interfaces for robotic laparoscopy are designed to receive user input to control the 4DOFs of laparoscopic instruments, plus jaw actuation, but lack the capability to actuate additional degrees of freedom should articulating or wristed instruments be used on the robotic system. This application describes a user interface having sufficient degrees of freedom to control operation of 6DOF instruments and/or to operate in accordance with true cartesian motion, but that also can be placed in a mode of operation in which the input handle moves with respect to a virtual fulcrum establish at the UI, thus allowing control of a 4DOF instrument using motions akin to those that would be used to manually move a laparoscopic instrument.

As described in application US 2013/0012930, the ability to understand the forces that are being applied to the patient by the robotically controlled surgical devices during minimally invasive surgery is highly advantageous to the surgeon. Communication of information representing such forces to the surgeon via the surgeon interface is referred to as "haptic feedback." In some systems, haptic feedback is communicated to the surgeon in the form of forces applied by motors to the surgeon interface, so that as the surgeon moves the handles of the surgeon interface, s/he feels resistance against movement representing the direction and magnitude of forces experienced by the robotically controlled surgical device. Forces represented can include both the forces at the tips of the robotically controlled devices and/or the forces being applied by the shaft of the robotically controlled device to the trocar at the entrance point to the body, giving the surgeon complete understanding of the forces applied to the device so s/he can better control the device during surgery.

The present application describes a powered 6DOF (or higher) haptic user interface (UI) that may be used by a surgeon to input surgeon commands for control of a 6DOF surgical device, and to receive force feedback (including orientation haptics) representing forces experienced by that surgical device. Many prior art haptic user interfaces do not provide orientation haptics. Those that do typically use a heavy gimbal mechanism with motors near where the user manipulates the user interface handle, cantilevered far from the base of the UI mechanism. The cantilevered mass of the gimbal/motor assembly requires that the other motors in the mechanism consume more power to provide haptic feedback (due to inertial loading) and perform gravity compensation (due to large moment loads). This also means that these other motors have to be larger in order to avoid overheating, or have to be mated to a gear reduction, which introduces backlash and makes the mechanism more difficult for the user to manipulate (due to mechanical disadvantage). Additionally, the increased inertia near the location where the user manipulates the user interface handle means that the user will have to overcome greater inertial forces in order to move the handle. Additionally, in other devices, the motors that are located at a distance from the base of the UI mechanism require electrical cables (power, sensors, etc.) to be routed some distance along the mechanism.

The mechanism described herein is capable of providing orientation haptic feedback to user while eliminating use of a powered gimbal mechanism, reducing cantilevered weight, simplifying electrical and mechanical cabling, and using smaller motors and reduced power consumption.

DETAILED DESCRIPTION

Figure 1:
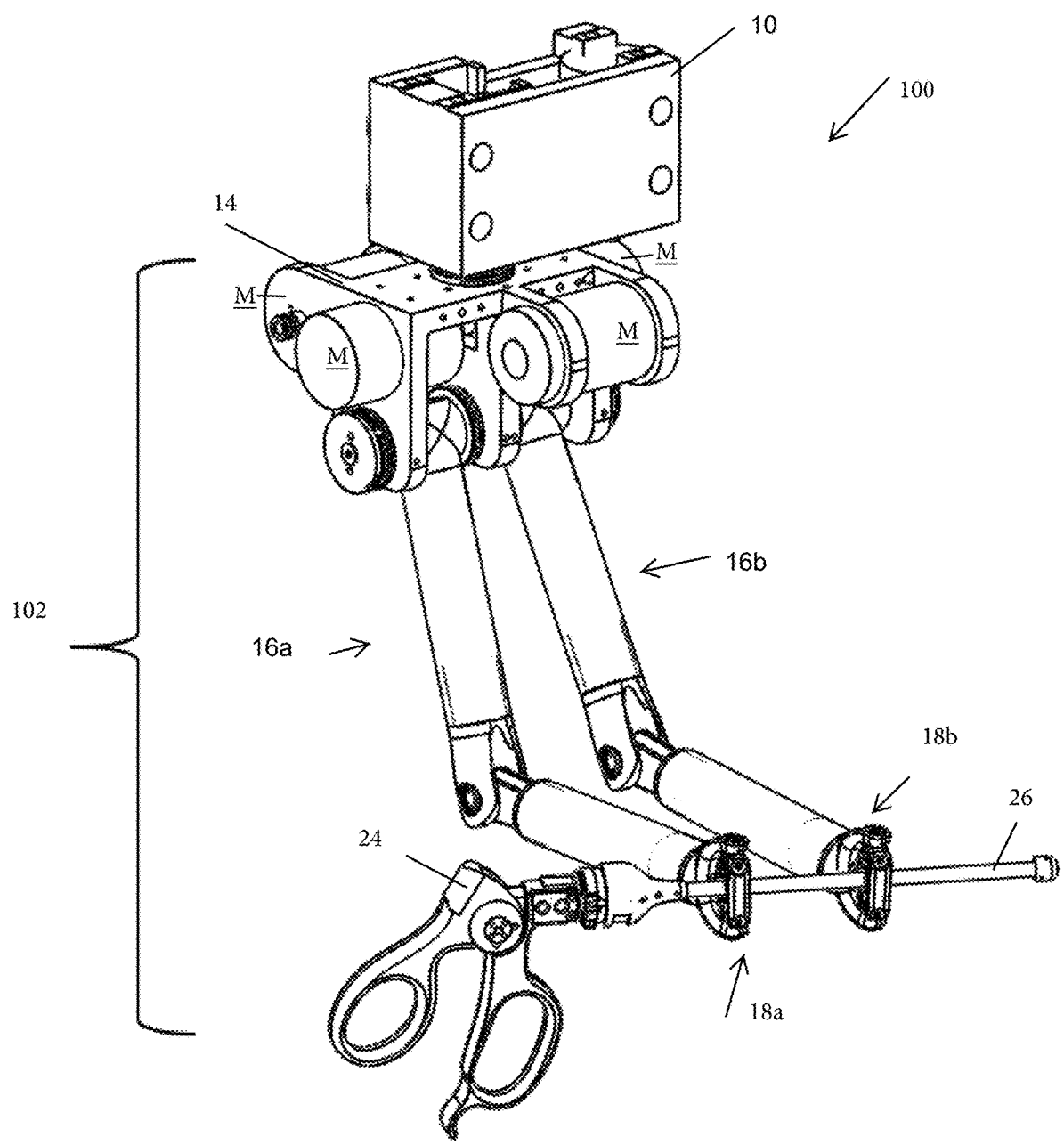
FIGS. 1 and 2 are perspective views of a powered user interface.

This application describes a user interface that is designed to be manipulated by a user to generate signals that are used to command motion of a robotically controlled device, and to provide haptic feedback to the user in six degrees of freedom. Note that this application will describe the user interface in the context of a robotic manipulator having a surgical instrument as the robotically controlled device, but it should be understood that the interface may be used for other types of robotically controlled devices.

The interface device is capable of providing a user experience similar to that of controlling a laparoscopic instrument and does so by virtually creating a haptic rotational center-of-motion (RCM) constraint at the UI using the haptic motors. In use the interface is preferably positioned at a surgeon console in which the surgeon sits or stands and manipulates the UI while observing an image of the surgical operating space within the body on an image display including, without limitation, a console-mounted or wearable image display.

The user interface is a six degree-of-freedom (DOF) mechanism containing electric motors that can provide haptic feedback to the user. The user manipulates the user interface by grasping a handle attached to the user interface. The position of any point rigidly attached to the handle, as well as the orientation of the handle, is determined based on the measured position of six joints. The haptic forces provided to the user are delivered by six electric motors. The position of the six joints is determined using sensors that are attached to the motors. The position and orientation of the handle is reconstructed (in software) from the measurements of all of the sensors. For example, the position along the x-ordinate depends on the positions of all six sensors, not just one.

The handle of the instrument is used to actuate the jaw (or other feature) of a robotically controlled surgical device/instrument, although this motion is not counted as one of the six DOFs mentioned above. However, it is independently actuated/measured by a motor/sensor that may be located in the handle.

The user interface is incorporated into a user workstation, which may include one or more such user interfaces, as well as a video display allowing the user to view images taken from a laparoscope or other type of camera disposed within the patient. In one implementation of the user interface 100, shown in FIGS. 1 and 2, a linkage system 102 is supported at the user workstation (not shown) by a base 10. Base 10 includes a base motor 12 (FIG. 2). A linkage assembly 14 is rotationally coupled to the base 10 such that operation of base motor 12 rotates the linkage 14 relative to the base 10. Two linkage arms 16a, 16b are mounted to the linkage 14. Each of the arms 16a, 16b comprises two active degrees of freedom and at least two passive degrees of freedom. In this embodiment, those active degrees of freedom are driven by four additional motors M mounted on the linkage 14 (labeled in FIG. 1). Additional active degrees of freedom allow roll about the handle axis and closure of the handles with respect to one another. The motors for these features are not shown. An additional passive degree of freedom allows the sliding of the handle shaft with respect to the end of one arm, although a second embodiment described below does not include this DOF.

Figure 2:
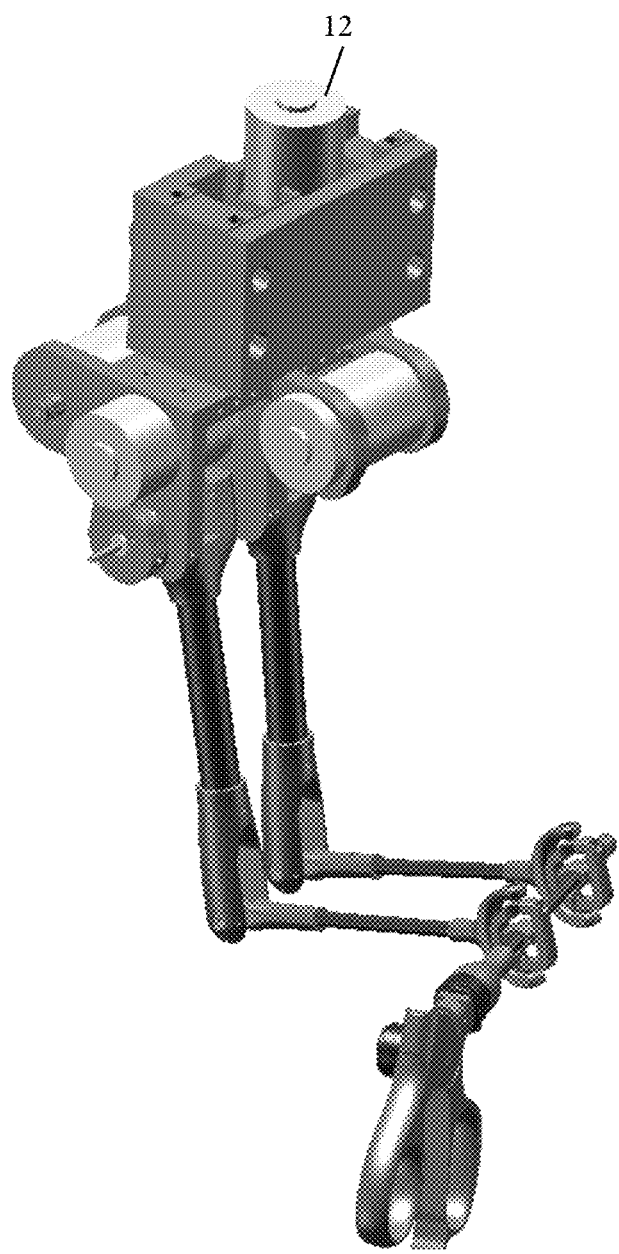
Figure 3:
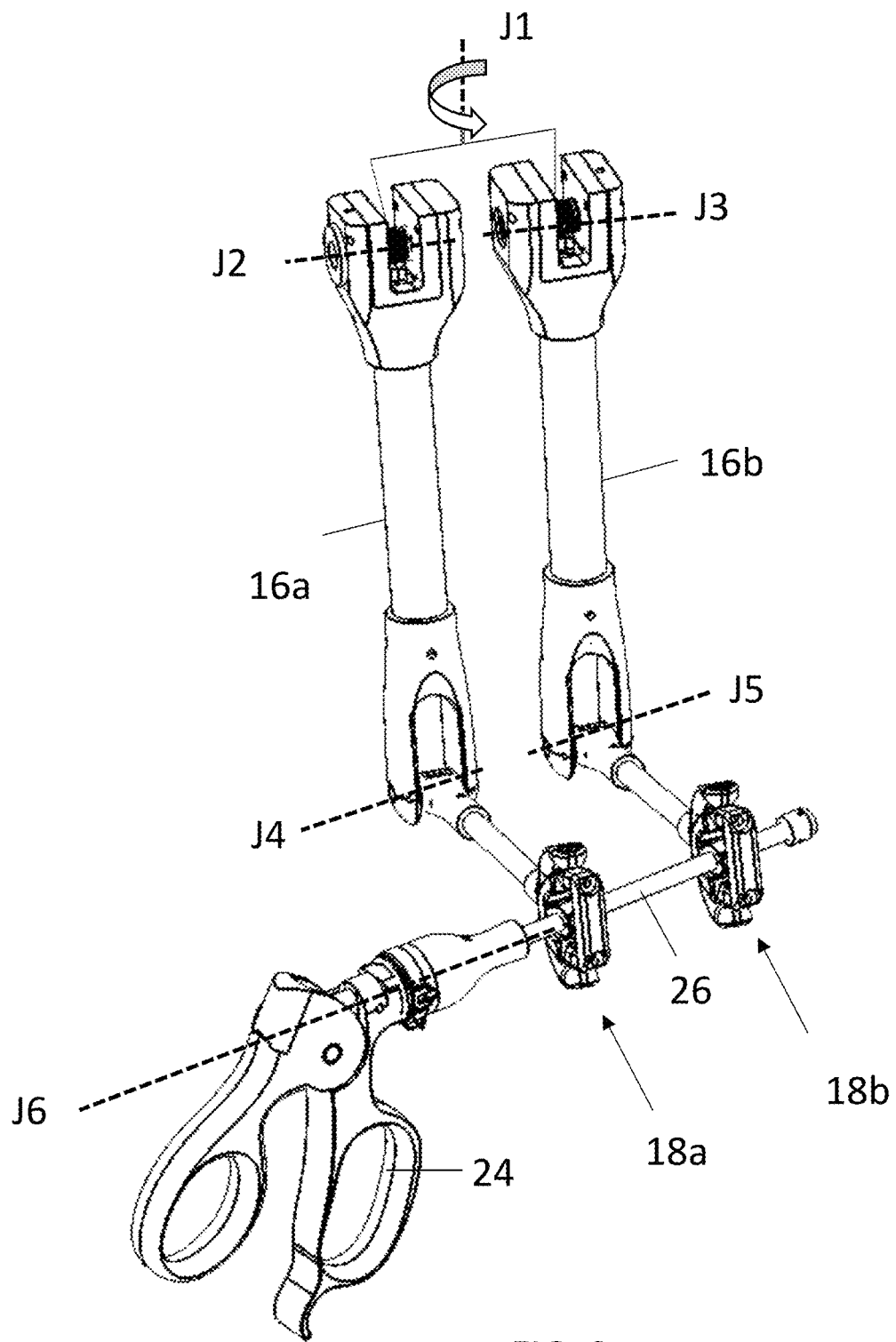
FIG. 3 schematically shows the powered and measured joints of the powered user interface shown in FIG. 1.

The kinematics of the UI will be best understood with reference to FIG. 3, which is similar to FIG. 1, but which does not show the base 10 and which shows linkage 14 only schematically. The location of the six joints J1-J6 of the user interface are shown, all of which are capable of being independently actuated and measured by their respective motors M and sensors (not shown). In this implementation, all six joints are revolute joints, and their axes of rotation are indicated by the direction of the dashed lines in the figure. Here the two two-bar linkages (each being one of the arms 16a, 16b) are shown schematically mounted upon linkage 14, which is a rotating platform rotatable relative to the base 10 (not shown). In this embodiment the arms 16a, 16b are parallel to one another, while in the second embodiment they are not fixed in a parallel relationship to one another. The rotating platform 14 is actuated/measured by J1. J2 and J4 actuate/measure the proximal (nearest to the handle) two-bar linkage 16a, while J3 and K5 actuate/measure the distal (furthest from the handle) two-bar linkage 16b. In this embodiment, the axes of J2-J5 are always parallel to one another. The four motors M (FIG. 1) that actuate/measure J2, J3, J4 and J5 are all mounted upon the platform 14 controlled by joint 1. J4 is actuated via cables or other means that are routed along the length of the link between J2 and J4. In one implementation, described in more detail below, these cables are routed around a pulley located at J2 that is concentric with the joint 2 axis. Therefore, motion of J2 affects the actuation/sensing of J3. This is compensated for in software. J3 and J5 are identical to J2 and J4 in their construction and compensation.

Figure 4:
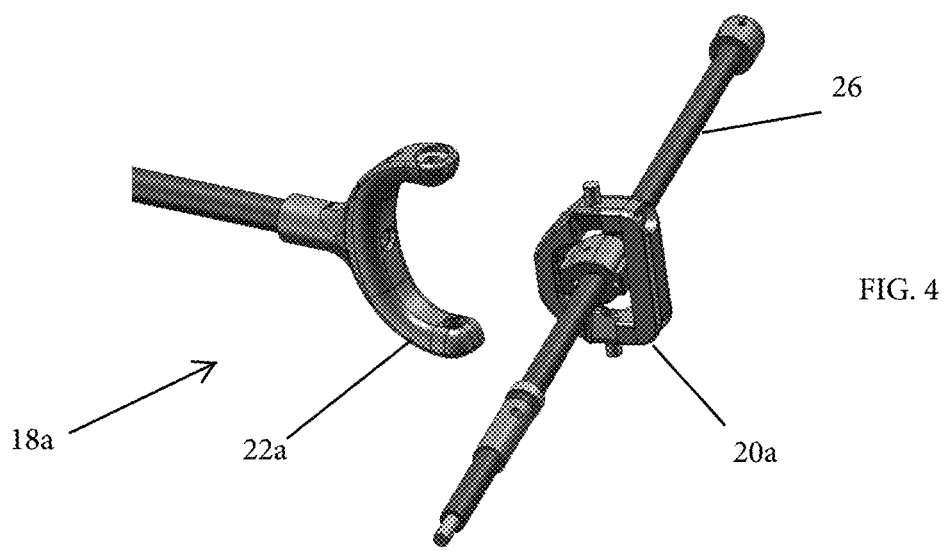
FIG. 4 is a partially exploded view of a gimbal interface of the interface of FIG. 1.

A handle 24 with a shaft 26 is coupled to the two-bar linkages. The end of each two-bar linkage 16a, 16b includes a passive gimbal 18a, 18b that allows the shaft 26 of the handle to yaw and pitch relative to the two-bar linkages 16a, 16b. See FIG. 4. In this embodiment, each gimbal 18a, 18b includes an inner ring 20a, 20b and an outer ring 22a, 22b (see reference numbers in FIG. 4). The shaft 26 of the handle 24 is fixed to the inner-most ring 20a of the proximal gimbal 18a. In the first embodiment, the shaft of the handle is able to slide freely through the inner-most ring 20b of the distal gimbal 18*b*. FIG. 4 is an exploded view showing the inner ring 20*a* and outer ring 22*a* of gimbal 18*a* along with a portion of shaft 26.

Referring again to FIG. 3, joint 6 can be measured/actuated in two different ways. Either a small motor/sensor assembly can be mounted to the shaft of the handle and used to actuate/measure joint 6, or joint 6 can be actuated/measured via cables routed along the links of the proximal two-bar linkage 16*a*. In the latter case, compensation for the motion of joints 2 and 4 is performed using software in order to accurately measure the motion about J 6.

Figure 5:
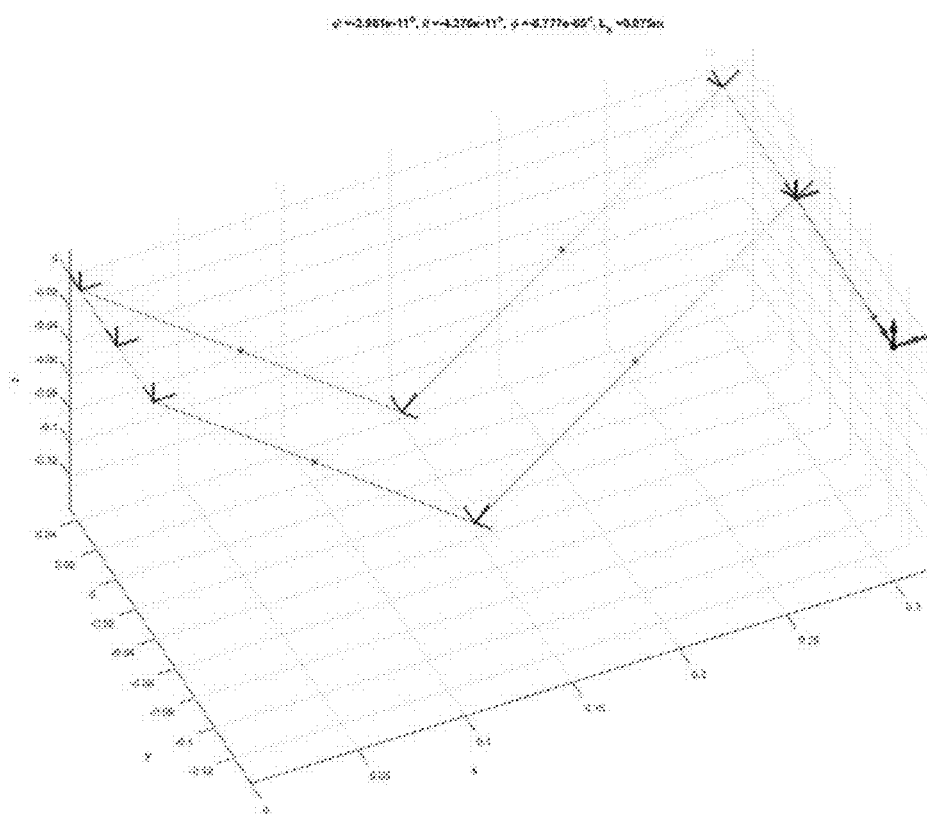
FIG. 5 is a kinematic diagram showing the degrees of freedom of the user interface of FIG. 1, with the right hand side of the drawing representing the handle, shaft and gimbals.

FIG. 5 is a kinematic diagram showing the degrees of freedom from the embodiment shown herein, with the right hand side of the drawing representing the handle 24, shaft 26 and gimbals 18*a*, 18*b* shown in the other drawings.

During use of the user interface, actuation of any combination of the motors (which, in use, results from the sensing of forces resulting from interactions between the surgical device under robotic control and surrounding structures) causes the user moving the handle 24 to feel resistance against movement in the DOFs.

Implementations that sense rotation about the roll axis (J6) for the purpose of receiving input used to control the robotic surgical instrument, but that do not provide haptic constraint or feedback for the roll axis as shown are also within the scope of the invention. Additional input devices or axes (passive, sensed, or sensed and actuated) may be added beyond those described above to provide additional control capability, redundant control capability, or increased range of motion and are within the scope of the invention. One example of this may be a prismatic joint along the shaft 26 that provides additional range of motion for insertion.

For each actuated degree of freedom, various mechanisms may be used to transmit motion from the motors to the center of the actuated degree of freedom. In one implementation, cables are used to transmit motion from the motors to the center of the actuated degrees of freedom. Differences in pulley size may be used to create a mechanical advantage. Cables, which may be metal, plastic, or a combination thereof, are wrapped around a set of pulleys or capstans and tensioned to bidirectionally translate motion. Cables provide the advantage of light weight and minimal backlash, both of which are important for a haptic interface.

Figure 6:
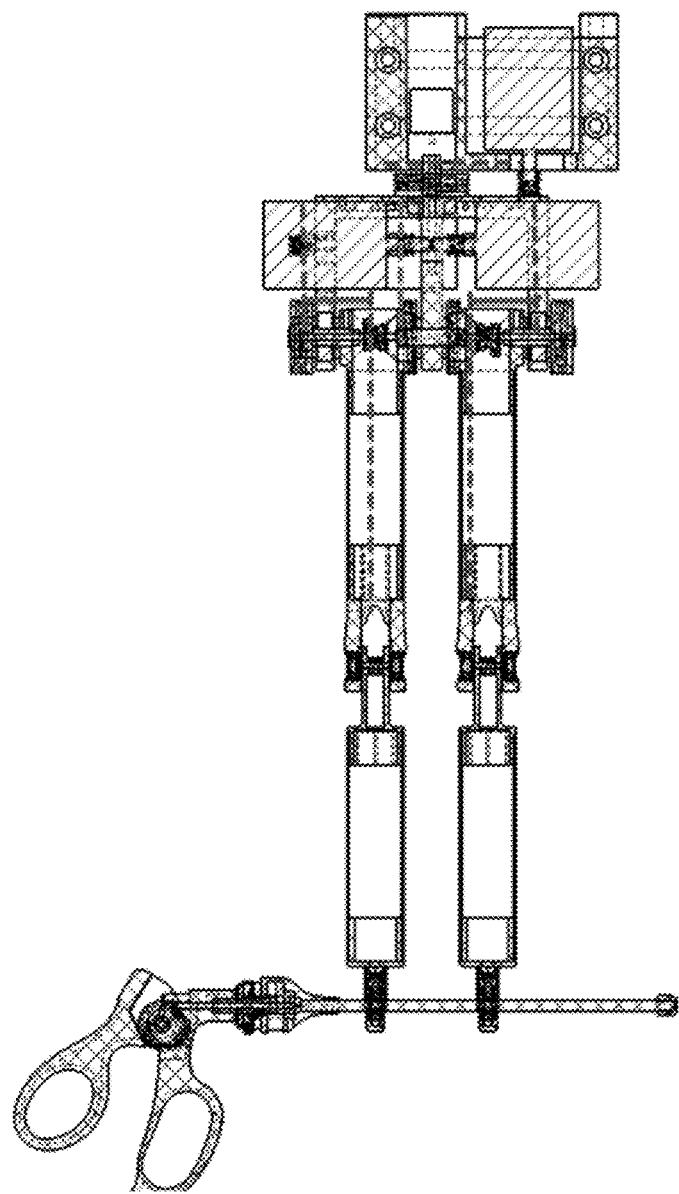
FIG. 6 illustrates cable routing of the interface of FIG. 1.

FIG. 6 is a cross-section view of the user interface shown in FIGS. 1-5, and further illustrates cable driving paths to the centers of the driven degrees of freedom for joints J1-5. Note that the common shaft(s) communicate from the outer pulleys, through the proximal axes to the inner pulleys that drive the cables to actuate the distal axes of each arm 16*a*, 16*b*. In other implementations, an additional cable or set of cables running through the linkage(s) may be used to actuate the rotational (roll) axis of the handle and/or the closure of the handle.

In alternative embodiments, gears are used to convey the motion from the motors to the axes. In some implementations, a combination of spur and bevel gears are used, but other gears, such as, but not limited to, spur gears, bevel gears, and helical gears. Features and components may be added to reduce backlash.

Figure 8:
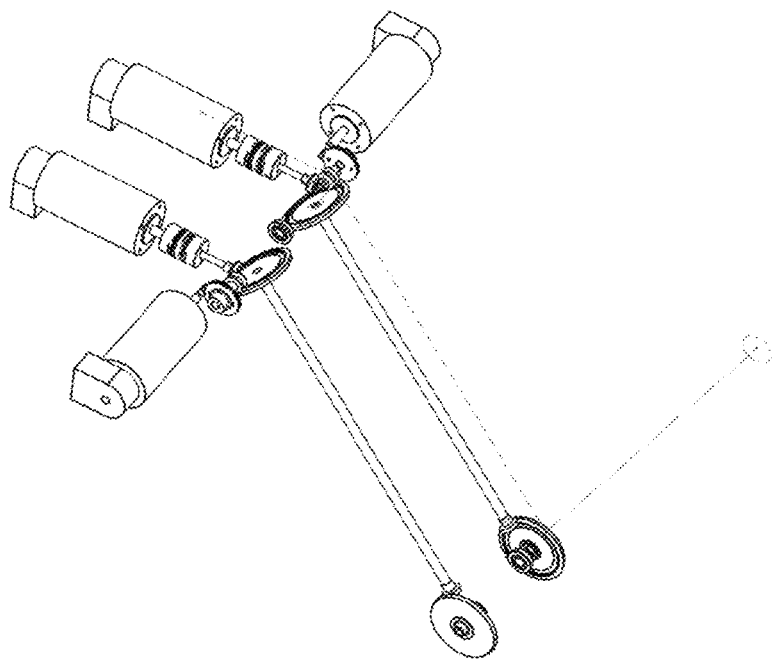
FIG. 8 illustrates the motors, gears, and shafts for a bevel gear implementation used to drive joints of the first or second embodiment. This drawing only shows the gears and shafts and does not show the linkage arms.

FIG. 8 illustrates the motors, gears, and shafts for a bevel gear implementation used to drive joints J2 through J5. Note that this drawing does not show the linkage arms 16*a*, 16*b*, only the gears and shafts. The dotted lines represent the position of two links of one of the linkage arms.

Figure 9:
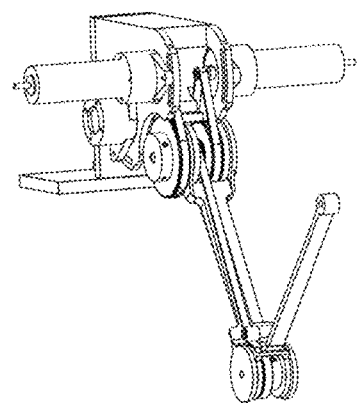
FIG. 9 illustrates use of belts and/or cables to transfer motion from the motors to the center of axes of motion in the first or second embodiment.

Referring to FIG. 9, in an alternative embodiment belts and/or cables are used to transfer motion from the motors to the center of axes of motion. In some implementations, the difference in pulley size is used to create a mechanical advantage. Timing belts may be used to reduce slipping, increasing positioning resolution and potential output torque. In the FIG. 9 embodiment, the paths of the belts are similar to those in the cable implementation shown in FIG. 6, but alternative belt routes may be used.

Figure 7:
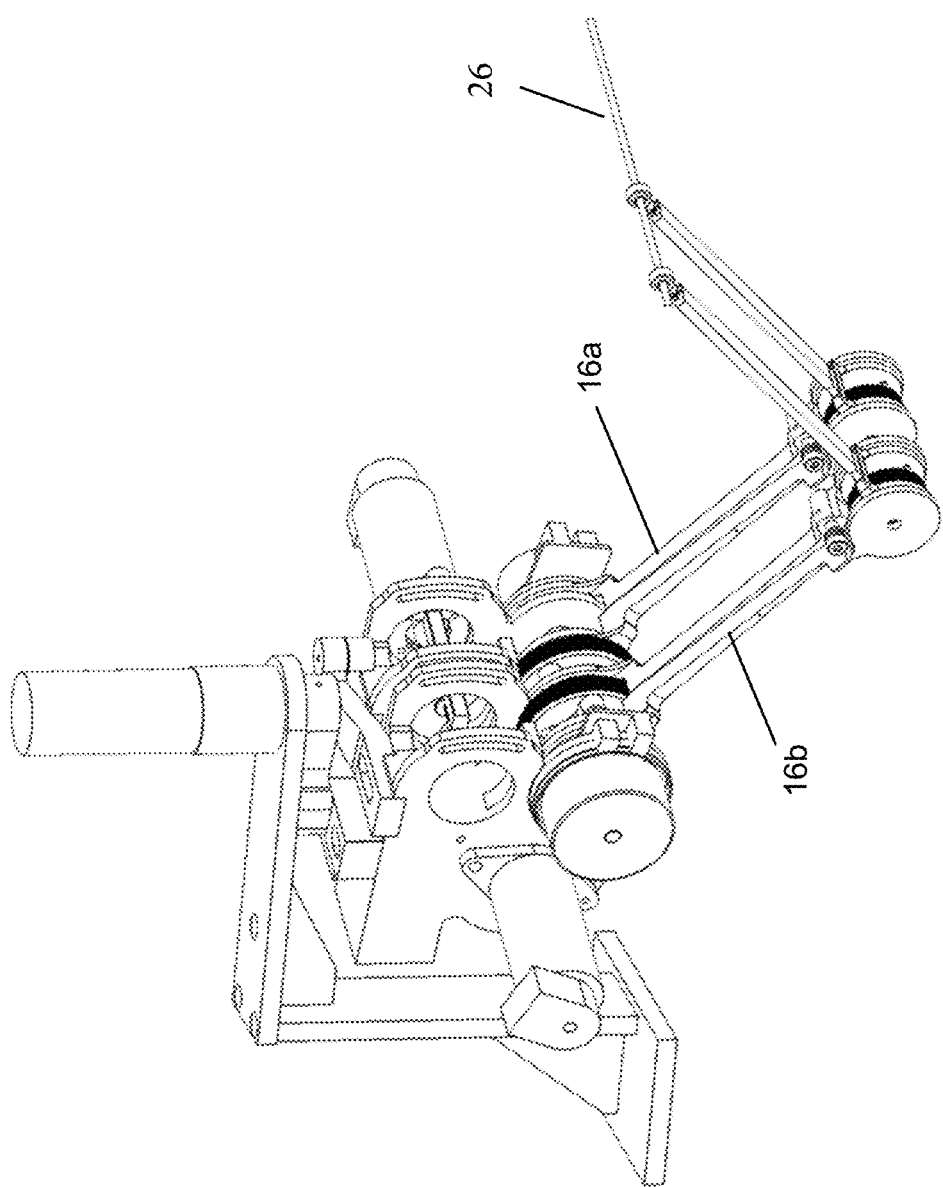
FIG. 7 shows a perspective view of a second embodiment of a powered user interface.

A second embodiment is shown in FIG. 7. The second embodiment differs from the first in that the handle shaft is not able to slide through the distal gimbal. Instead, the handle shaft is constrained at the distal gimbal. An additional DOF is instead added at the shoulder joint of the distal arm 16*b*. This additional DOF is in the form of a slight pivot in a horizontal plane, which allows that shoulder joint to thus both rotate in a horizontal plane and moving up/down at J3 (this latter DOF also being present in the first embodiment). This allows a shorter handle shaft to be used and it eliminates a sliding constraint in favor of a rotating constraint.

Although two examples of 6DOF embodiments are shown, various other embodiments within the scope of this disclosure can employ alternative configurations for DOFs. For example:

In an alternative embodiment, a first, two-link, arm may be used to mechanically (rigidly or haptically) define a remote center of motion (RCM) through which a shaft slides, and a second arm having at least three degrees of freedom may be used to define the position of the end of the instrument shaft. With the addition of a roll axis control similar to that defined above, this combination of degrees of freedom may also be used to define the motion in six-degrees of freedom. Having a visibly fixed remote center of motion may provide additional familiarity to a laparoscopic surgeon familiar with inserting an instrument shaft through a trocar.

In another implementation, a pair of two-link arms on separately-actuated rotational bases may be used to define six-degree of freedom motion.

It should also be noted that alternative linkages to those shown and described in this application may instead be used as described here to input and define motion in six degrees of freedom.

Control of 4DOF System using a Greater than 4DOF UI

Another advantage of the disclosed system is that it is one that allows a single user interface design to be used to control a robot in different ways, e.g. laparoscopic or true Cartesian motion. As discussed in the Background section, some robotic surgical systems control laparoscopic surgical devices moveable in 4DOF, while other robotic surgical systems control surgical devices moveable in more than 4DOF, such as 6DOF. The disclosed haptic interface is one type of powered user interface that can be used to control either type of system, although it should be understood that the method may be practiced using various other UI designs having more than 4DOFs.

In accordance with this method, a UI having more than 4 DOFs can be operated to deliver input used to control a 4DOF surgical device without requiring the user to physically constrain his/her movement of the handle to mimic laparoscopic instrument motion. Instead, the actuators used for haptic feedback are used to constrain the user interface such that the handle manipulated by the user moves only in the relevant 4DOFs.

The four degrees of freedom necessary to control a 4DOF laparoscopic device are yaw and pitch (each with respect to a fixed fulcrum), roll and insertion. The UI described herein may be operated in a 4DOF mode of operation in which the handle motion relative to the base is limited to yaw, pitch, roll and insertion. Note that jaw open-close operation is not considered a degree of freedom, so it should be understood that, when motion is limited to these four DOFs, jaw open-close can be permitted. When the UI is operated in the 4DOF mode of operation, a virtual fulcrum or rotational center of motion (RCM) is created in the UI workspace. Note that the virtual RCM can be located at any point in the workspace. It may be created at a point that is arbitrarily selected by the system, or user-selected in response to a prompt, or pre-set at a default setting (and optionally changeable by the user), or determined or set in some other way.

Figure 10:
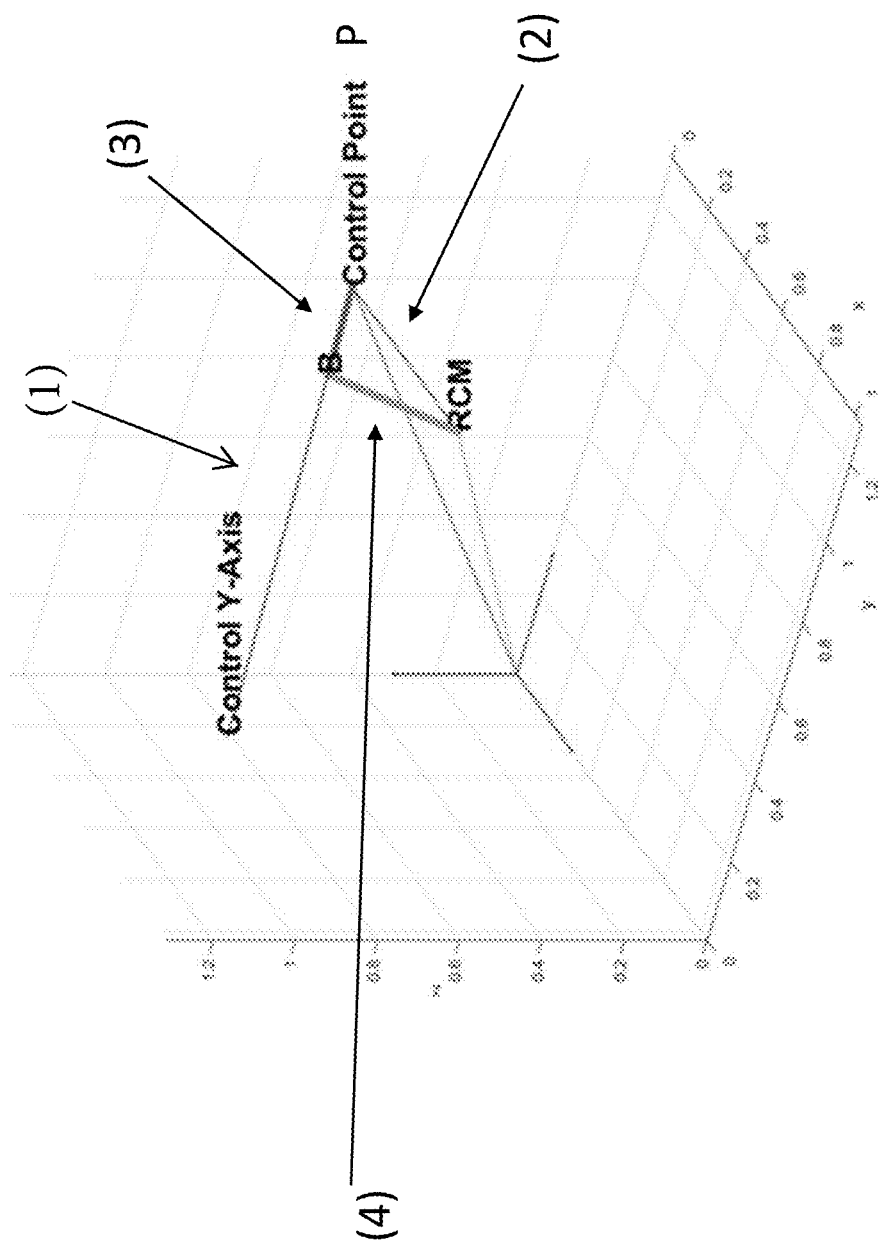
FIG. 10 depicts RCM constraint algorithms that may be used in methods for operating the 6DOF (or higher) user interface in a 4DOF mode.

Referring to FIG. 10, operation in the 4DOF mode of operation causes the actuators of the UI to orient the control Y-axis (line 1 shown in FIG. 10) which points in the direction of the handle of the UI) to pass through the RCM point, so that the handle of the instrument is caused by the actuators to always point towards the RCM constraint. Thus once the virtual fulcrum is set (or it may be pre-set at a default point) the haptic actuators then generate corrective moments that will manipulate the orientation of the UI handle such that its insertion axis passes through the virtual fulcrum point. The user moving the handle thus experiences laparoscopic-style motion constrained relative to the virtual fulcrum. Thus in this mode, the handle motion relative to the base is limited by the actuators to pitch and yaw of the shaft of the handle relative to the virtual fulcrum, axial roll about the longitudinal axis of the handle shaft ("roll"), and translation along the handle shaft ("insertion").

Using a first embodiment, the corrective moment is computed based on the error between the actual orientation and the desired orientation (one whose insertion axis intersects the virtual fulcrum). Referring to FIG. 10, the corrective moment is proportional to the orientation error, and also contains some viscous damping to prevent instability. In FIG. 10, the virtual fulcrum is labeled "RCM" (rotational center of motion) and the UI handle is attached to control point P (a point located on the user interface, such as on the handle, the position of which is known based on the kinematics of the user interface mechanism). The method causes the y-axis (line 1) at point P, which is the insertion axis and runs in the direction of the handle, to pass through the virtual RCM.

To do this, an algorithm is employed to determine the difference in direction between the control y-axis (line 1) and the vector from the control point P to the RCM (line 2 in FIG. 10). The angle that is determined becomes an error which generates torque that is applied to bring that difference in direction to zero.

The corrective moment is computed as $$\vec{\tau}_{corr} = k_s \vec{\epsilon} - k_d \vec{\omega} \quad (7)$$

Where $\vec{\epsilon}$ is the orientation error, $\vec{\omega}$ is the measured angular velocity of the handle, and $k_s$ and $k_d$ are the stiffness and damping gains, respectively.

This method allows for the consolidation of UI mechanisms used to control multiple types of devices. Rather than requiring separate UI's for different surgical systems (eg 4DOF UI to control a laparoscopic robot such as that described in WO 2007/088206, WO 2008 049898, and a 6DOF (or greater) UI for systems such as a laparoscopic robot using instruments that include additional degrees of freedom such as articulation or wristed motion, or a true Cartesian motion robotic surgical system, a single 6DOF (or greater) UI may be used with each type of system by using haptic actuators to artificially constrain the motion of the UI mechanism such that it feels to the user to be a 4DOF UI when 4DOF is needed.

This method thus allows for a greater-than-4DOF UI to be used to control a 4DOF device (to mimic laparoscopic motion). It also allows for creation of a virtual RCM which can be placed arbitrarily within the workspace and can be moved at any point before or during a procedure, if desired. For example, the system might have an RCM pre-set at a default position, but include an RCM setting mode in which the user can select a different RCM for a particular one of the instruments.

When in the RCM setting mode, the user could, for example, move the corresponding handle to a certain point in space and then give input to the system that triggers the system to calculate where the handle is positioned. The input device could be a switch or other form of input on the UI handle, a keypad, keyboard or other form of input device at the console, a sensor for voice activated input, or any other input device that could be used to select RCM setting mode.

In an alternative approach, an impedance controller is implemented to force the motion of the user interface to always pass through the RCM. As with the first approach, this electronically constrains the motion of the powered user interface device such that the motion of the user interface handle will mimic laparoscopic motion.

Referring again to FIG. 10, using this alternative method an RCM constraint algorithm determines the torques that need be applied to the actuators of the user interface to force the y-axis of the control axes (a set of coordinate axes that are located on the user interface and whose orientation is known based on the kinematics of the user interface mechanism) to intersect the virtual RCM. Steps of the RCM constraint algorithm including the following:

(1) Computing the vector from the control point P (a point located on the user interface, such as on the handle, the position of which is known based on the kinematics of the user interface mechanism) to the RCM (line 2 in FIG. 10), and find the projection of that vector onto the y-axis of the control axes (line 3 in FIG. 10) The point at which the projection intersects the y-axis (line 1) of the control axes will become a second control point, point B.

(2) Finding the vector connecting the RCM and point B calculated in step 1 (line 4 in FIG. 10). This vector represents the point of closest approach of the control y-axis and the RCM.

(3) Implementing an impedance controller that will apply a force to the user interface (via the user interface actuators) that is in the direction of, and having a magnitude that is proportional to, the vector obtained in step 2. The impedance controller can also include damping that is proportional to the rate of the change of the vector obtained in step 2, as well as inertial terms to compensate for the accelerating mass of the user interface.

The below equations describe this above controller (excluding the inertial terms):

$$F_{actuators} = J_B^T (K r_{RCM/B} b \dot{r}_{RCM/B})$$

Where $J_B^T$ is the transpose of the displacement Jacobian of control point B, K is a 6×6 diagonal stiffness matrix, b is a 6×6 diagonal damping matrix, and $r_{RCM/B}$ is a vector from the RCM to point B (line 4 of FIG. 10B).

While the above methods are described in the context of enabling a single user interface configuration to be used to control a surgical robotic system in more than one way, e.g. laparoscopic or true Cartesian motion, these methods are also useful for creating arbitrary constraints in the user interface work space. For example, they can be used to force the user interface to re-trace motions that have been previously executed for pre-programmed. This can be useful in surgeon training, among other things.

The above method may be further enhanced by attaching the virtual RCM to the user interface mechanism in the sense that it will move with the user interface mechanism. In this way the user will experience the presence of a fulcrum (thus feeling familiar to a laparoscopic surgeon) but will be permitted to relocate the fulcrum to achieve more dexterous motion and greater range of motion of the surgical instrument being controlled.

In accordance with this enhanced method, the moveable RCM constraint algorithm determines the torques that need be applied to the actuators in the user interface to force the y-axis of the control axes (a set of coordinate axes that are located on the user interface and whose orientation is known based on the kinematics of the user interface mechanism) to intersect the virtual RCM in the manner described above. Additionally, the location of the virtual RCM is constantly updated by an RCM update algorithm that will move the RCM in the direction of insertion of the user interface. In that regard the motion is similar to that of a wheelbarrow—it only moves in the direction that it is pointing, and the can pivot about the "wheel" to commence movement in a different direction. Once movement has begun, the pivot point/RCM (front wheel) moves with the handle.

An example of the RCM update algorithm is as follows:
(1) Compute the vector from the control point P (a point located on the user interface that has a known position based on the kinematics of the user interface mechanism) to the RCM (line 2 in FIG. 10B), and find the projection of that vector onto the y-axis of the control axes (line 3 terminating at point B in FIG. 10B).
(2) Advance the RCM in the direction of the y-axis of the control axes by adding the projection vector computed in step (1) to the current location of the RCM.

Meanwhile, as described above, an impedance controller will apply a force to the user interface (via the user interface actuators) that will tend to bring the y-axis of the control axes to intersect the RCM. This will have the effect of providing a laparoscopic feel to the user. The addition of the moveable RCM will then allow the user to "steer" the RCM and ultimately locate the instrument in more favorable positions for performing surgical tasks.

All prior patents and patent applications referenced herein, including for purposes of priority, are incorporated herein by reference.

We claim:

1. A method of using a powered user interface to control a robotic surgical system having a manipulator and a surgical instrument mounted to the manipulator, including:
   generating input signals in response to movement of a handle of a user interface, the handle coupled to a base;
   causing movement of the manipulator or surgical instrument in accordance with the input signals;
   selectively operating actuators of the user interface in accordance with:
      a first mode of operation in which the actuators are operated to constrain motion of the handle to permit motion of the handle in only 4DOF with respect to the base, and
      a second mode of operation in which the actuators permit motion of the handle in at least 6DOF with respect to the base.

2. The method of claim 1, wherein in the first mode of operation the motion is constrained to the DOFs of pitch, yaw, roll and insertion.

3. The method of claim 2, wherein the pitch and yaw motion is constrained with respect to a virtual fulcrum in a work space of the user interface, and wherein insertion motion is constrained along an axis passing through the virtual fulcrum.

4. The method of claim 1, wherein the first mode of operation simulates laparoscopic motion of the handle with respect to a virtual fulcrum in a work space of the user interface.

5. The method of claim 4, wherein the handle includes an insertion axis and wherein, in the first mode of operation, the actuators generate corrective moments to maintain the orientation of the insertion axis such that it passes through the virtual fulcrum.

6. The method of claim 4, wherein the handle includes an insertion axis and wherein, in the first mode of operation, the system implements an impedance controller to cause the insertion axis to remain oriented passing through the virtual fulcrum.

7. The method of claim 1, further including determining, based on measurements obtained using sensors at the manipulator, an estimate of forces exerted onto the instrument, and operating the actuators to deliver at the handle haptic feedback corresponding to the estimated forces.

8. The method of claim 3, further including performing a virtual fulcrum setting mode including the steps of:
   prompting a user to give input to the system selecting a desired point in space for the virtual fulcrum,
   receiving user input corresponding to a selected point; and
   setting the selected point in space as the virtual fulcrum.

9. The method of claim 8, wherein the virtual fulcrum setting mode is performed at a time when movement of the manipulator is not being actively controlled using input from the user input device.

10. The method of claim 8, wherein the virtual fulcrum setting mode is performed at a time when movement of the manipulator is being actively controlled using input from the user input device, with the virtual fulcrum being constantly updated during active control of the manipulator using input from the user input device.

11. The method of claim 1, wherein the causing step comprises causing movement of the manipulator in accordance with the input signals, said movement causing the surgical instrument to move.

12. The method of claim 1, wherein the causing step comprises causing movement of the surgical instrument in accordance with the input signals.

13. A powered user interface for a robotic surgical system having a manipulator and a surgical instrument mounted to the manipulator, the powered user interface including:
   a base;
   a handle mounted to the base, the handle moveable relative to the base in at least six degrees of freedom;
   actuators coupled between the base and the handle;
   a computing device programmed to selectively operate the actuators in accordance with:
      a first mode of operation in which the actuators are operated to constrain motion of the handle to limit said motion to only 4DOF with respect to the base, and
      a second mode of operation in which the actuators permit motion of the handle in at least 6DOF with respect to the base.

14. The user interface of claim 13, wherein in the first mode of operation the motion is constrained to the DOFs of pitch, yaw, roll and insertion.

15. The user interface of claim 13, wherein the pitch and yaw motion is constrained with respect to a virtual fulcrum in a work space of the user interface, and wherein insertion motion is constrained along an axis passing through the virtual fulcrum.

16. The user interface of claim 13, wherein the first mode of operation simulates laparoscopic motion of the handle with respect to a virtual fulcrum in a work space of the user interface.

17. The user interface of claim 16, wherein the handle includes an insertion axis and wherein, in the first mode of operation, the actuators generate corrective moments to maintain the orientation of the insertion axis such that it passes through the virtual fulcrum.

18. The user interface of claim 16, wherein the handle includes an insertion axis and wherein, in the first mode of operation, the system implements an impedance controller to cause the insertion axis to remain oriented passing through the virtual fulcrum.

19. The user interface of claim 13, wherein the computing device is further programmed to determine, based on measurements obtained using sensors at the manipulator, an estimate of forces exerted onto the instrument, and to operate the actuators to deliver at the handle haptic feedback corresponding to the estimated forces.

20. The user interface of claim 15, wherein the computing device is further programmed to perform a virtual fulcrum setting mode in which the computer device:
    generates a prompt prompting a user to give input to the system selecting a desired point in space for the virtual fulcrum,
    receives user input corresponding to a selected point, and
    sets the selected point in space as the virtual fulcrum.

\* \* \* \* \*